United States Patent [19]

Swanson

[11] Patent Number: 4,969,908
[45] Date of Patent: Nov. 13, 1990

[54] LUNATE IMPLANT AND METHOD OF STABILIZING SAME

[76] Inventor: Alfred B. Swanson, 2945 Bonnell, S.E., Grand Rapids, Mich. 49506

[21] Appl. No.: 510,097

[22] Filed: Apr. 17, 1990

Related U.S. Application Data

[62] Division of Ser. No. 360,430, Jun. 2, 1989.

[51] Int. Cl.$^5$ .............................................. A61F 2/42
[52] U.S. Cl. ...................................................... 623/21
[58] Field of Search ........................................... 623/21

[56] References Cited

U.S. PATENT DOCUMENTS

| | | | |
|---|---|---|---|
| 3,924,276 | 12/1975 | Eaton | 623/21 |
| 4,164,793 | 8/1979 | Swanson | 623/21 |
| 4,198,712 | 4/1980 | Swanson | 623/21 |
| 4,450,591 | 5/1984 | Rappaport | 623/21 |

Primary Examiner—Alan Cannon
Assistant Examiner—Stephanie Iantorno
Attorney, Agent, or Firm—Price, Heneveld, Cooper, DeWitt & Litton

[57] ABSTRACT

A lunate implant includes a one-piece, at least semi-rigid body defining a triquetrum face, a scaphoid face, a cupped, concave, distal surface adapted to articulate with the capitate bone, a proximal surface, a palmar surface and a dorsal surface. A pair of spaced, generally parallel suture passages extend between and open through the triquetrum and scaphoid faces. A pair of sutures are stitched to ligaments of the wrist. The ends of the sutures are passed through the suture passages so that one of the sutures has ends extending away from the triquetrum face and the other suture has ends extending away from the scaphoid face. The ends are grasped and the lunate implant is pulled down into the desired position in the distal carpal row of the wrist. The sutures are tied adjacent the implant to stabilize and position the implant.

5 Claims, 3 Drawing Sheets

Figure 1:
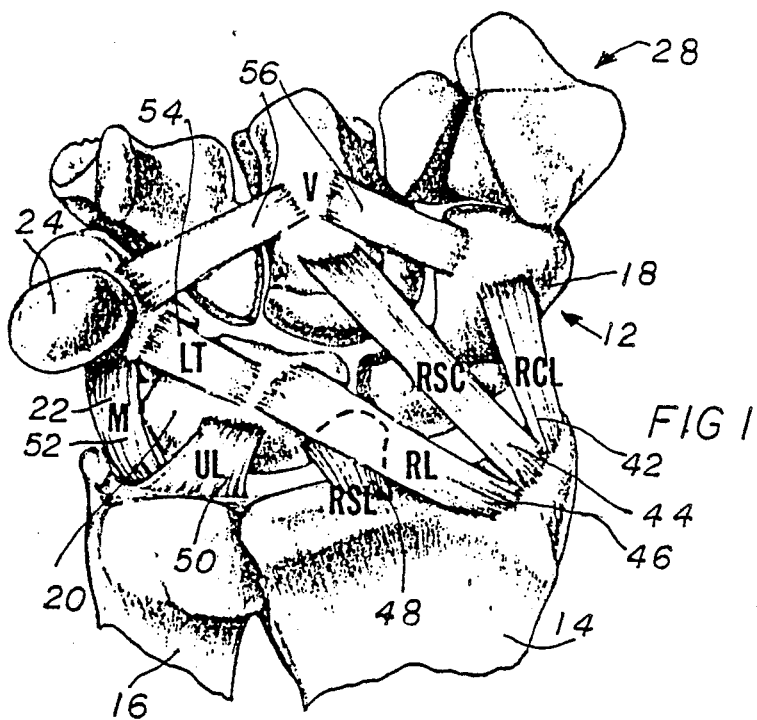
Figure 3:
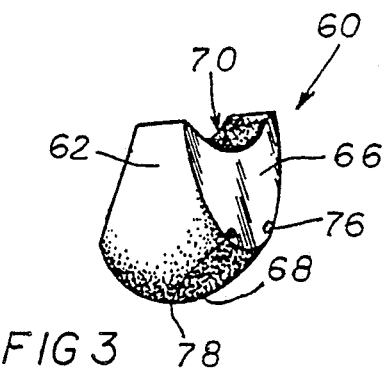
Figure 2:
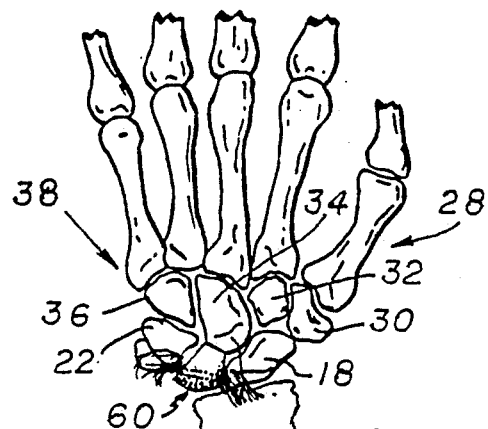
Figure 4:
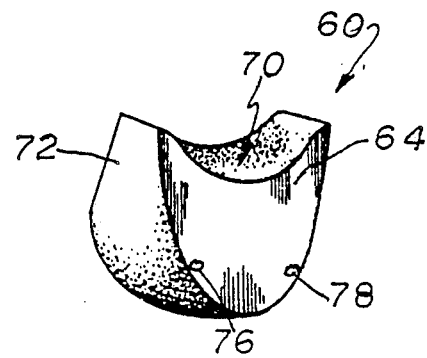
Figure 6:
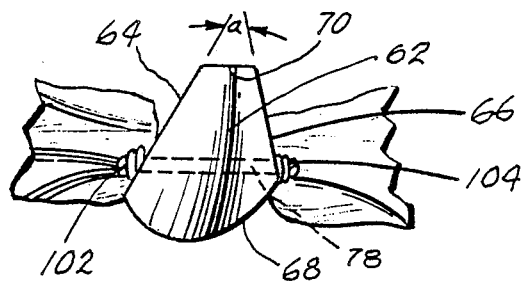

LUNATE IMPLANT AND METHOD OF STABILIZING SAME

BACKGROUND OF THE INVENTION

The present invention relates to arthroplastic reconstruction of the human joints and more particularly to implant resection arthroplasty of the wrist joint. ·

Surgical treatments of arthritis and similar conditions of the wrist joint have included intercarpal fusion, wrist fusion, local resection, proximal row carpectomy, bone grafting, radial styloidectomy, radial shortening or ulnar lengthening and soft tissue interposition arthroplasty. Fusion procedures affect stability, power and mobility of the wrist. Local resection procedures, which involve removal of bone, are complicated by migration of adjacent carpal bones into the space left by the resection which results in unwanted instability.

Various forms of flexible implants formed from silicone rubber have been developed to replace the lunate bone of the carpal row. Such implants are designed to act as articulating spacers capable of maintaining the relationship of adjacent carpal bones after excision of the lunate while preserving mobility of the wrist. An example of one such prior lunate implant is found in U.S. Pat. No. 4,164,793, entitled LUNATE AND IMPLANT and issued on Aug. 21, 1979 to the present inventor. The implant disclosed therein includes a one piece body of resilient material defining a planar triquetrum face. The face has a generally U-shape in plan and includes a stabilizing stem extending outwardly from and perpendicular thereto. The implant body, in addition, defines a scaphoid face, a cupped, concave, smooth distal surface, a proximal surface, a dorsal surface and a palmar surface. The stem extending from the triquetrum face is adapted to be inserted into an opening formed in the triquetrum bone. The stem helps in stabilizing the bone and retaining it in the correct position.

In certain situations, it has been determined that a semi-rigid or a rigid, metal implant is advisable. With a rigid material, a stabilizing stem cannot be inserted into an adjacent bone. The rigid stem could cut or damage adjacent bone structures. In certain situations, the stabilizing stem of the flexible implants has caused some erosion. It would be advantageous to avoid having to enter adjacent bone structures. Heretofore, proper stabilization of the implant has not always been readily achievable.

SUMMARY OF THE INVENTION

In accordance with the present invention, the aforementioned problems are substantially eliminated. Essentially, a lunate implant fabricated from a semi-rigid or rigid material such as a titanium alloy is provided. The implant is configured to define a triquetrum face, a scaphoid face, a cupped, concave surface configured to articulate on the head of the capitate, a proximal surface, a palmar surface and a dorsal surface. The implant body further defines a plurality of suture passages extending in spaced relationship between and through the triquetrum and scaphoid faces. The lunate implant is stabilized by suturing to two adjacent ligaments of the wrist. A suture is stitched to a ligament and the ends thereof are passed through the suture passages so that they extend away from the triquetrum face. Another suture is stitched to another adjacent ligament and the ends passed through the suture passages so that they extend away from the scaphoid face. The ends of these sutures are grasped and the lunate implant may be pulled down into position. The sutures are then tied to define knots adjacent the respective scaphoid and triquetrum faces. The knot arrangement and suture technique stabilizes the rigid implant. Problems heretofore experienced with stabilizing stems, bone cutting, erosion, instability and the like are eliminated.

BRIEF DESCRIPTION OF THE DRAWINGS

FIG. 1 is a fragmentary, anterior view of the wrist joint showing the distal and proximal carpal rows and the extrinsic ligaments of the wrist;

FIG. 2 is a fragmentary, posterior view showing the wrist and a portion of the hand;

FIG. 3 is a perspective view of the implant showing the scaphoid face thereof;

FIG. 4 is a perspective view of the implant in accordance with the present invention showing the triquetrum o medial face thereof;

FIG. 5 is an enlarged, fragmentary, plan view showing the method of stabilizing the implant in accordance with the present invention;

FIG. 6 is a fragmentary, top plan view showing the implant sutured in position in the wrist; and FIGS. 7 and 8 show the positioning of the implant and method of stabilizing the implant in the wrist.

DETAILED DESCRIPTION OF THE PREFERRED EMBODIMENT

With reference to the drawings, FIGS. 1 and 2 illustrate the human wrist and extrinsic ligaments. As shown, the bones that make up the wrist joint include a proximal carpal row 12 adjacent the radius bone 14 and the ulnar bone 16. The proximal carpal row includes a scaphoid bone 18, a lunate bone 20, a triquetrum bone 22 and a pisiform bone 24. Lunate bone 20 articulates proximally with the radius, distally with the capitate and hamate bones, laterally with the scaphoid bone and medially about the triquetrum bone. The proximal carpal row of the wrist and the distal radius define the radial carpal joint. The wrist further includes a distal carpal row 28. The distal carpal row includes a trapezium bone 30, a trapezoid bone 32, a capitate bone 34 and a hamate bone 36. A midcarpal joint 38 of the wrist extends between the distal and proximal carpal rows.

As illustrated in FIG. 1, the carpal bones are held together by short interosseous ligaments. The ligaments define a symmetrical pattern due to insertions into the scaphoid, lunate, triquetrum and capitate bones. The ligaments include the radial collateral ligament (RCL) 42, the radioscaphocapitate ligament (RSC) 44, the radiolunate ligament (RL) 46, the radioscapholunate ligament (RSL) 48, the ulnolunate ligament (UL) 50, the ulnocarpal meniscus homologue (M) 52, the lunotriquetral ligament (LT) 54 and the deltoid ligament (V) 56. The ulnar collateral and radial collateral ligaments provide lateral support of the wrist. In addition, palmar radial carpal and dorsal radial carpal ligaments maintain support of the carpal area. The fibers of the palmar radial carpal ligament extend distally and obliquely from the radius, the triangular fibro-cartilage and styloid process of the ulna.

In accordance with the present invention, the lunate bone is replaced with a lunate implant 60 (FIG. 2). Implant 60 is a one-piece body which includes a posterior or dorsal surface 62, a triquetrum face or medial surface 64, a scaphoid face or lateral surface 66, a proximal surface 68, a distal surface 70 and an anterior or palmar surface 72 (FIGS. 3 and 4). Surfaces 66, 64 are planar and define an included angle "a" (FIG. 6). Angle "a" opens from the distal surface 70 to the proximal surface 68. Surfaces 64, 66 are adapted to abut against and articulate with the triquetrum and the scaphoid bones, respectively. These surfaces are generally U-shaped in plan. Distal surface 70 of implant 60 is concave and smoothly cupped in shape. Surface 70 defines a capitate articulating surface adapted to engage the head of the capitate bone 34.

The configurations of the surfaces of implant 60 are as disclosed in the aforementioned U.S. Pat. No. 4,164,793. Implant 60, however, does not have a stabilizing stem. In addition, implant 60 is formed with a pair of spaced, generally parallel suture passages 76, 78. The suture passage extend immediately adjacent the edges of the peripheries of faces 64, 66 and adjacent the surfaces 62, 72 and the proximal surface 68. The implant of the subject invention is fabricated from a semi-rigid or rigid material, such as a medical grade titanium. With a metal implant, a stabilizing stem would cut bone and cannot be employed to stabilize and position the implant within the carpal row. As set forth in U.S. Pat. No.4,164,793, the disclosure of which is hereby incorporated by reference, implant 60 is provided in a variety of graduated sizes.

Figure 5:
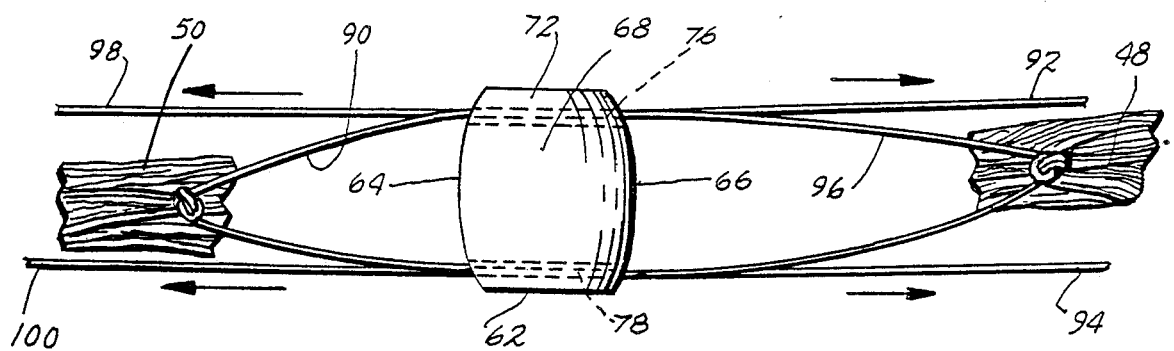
Figure 7:
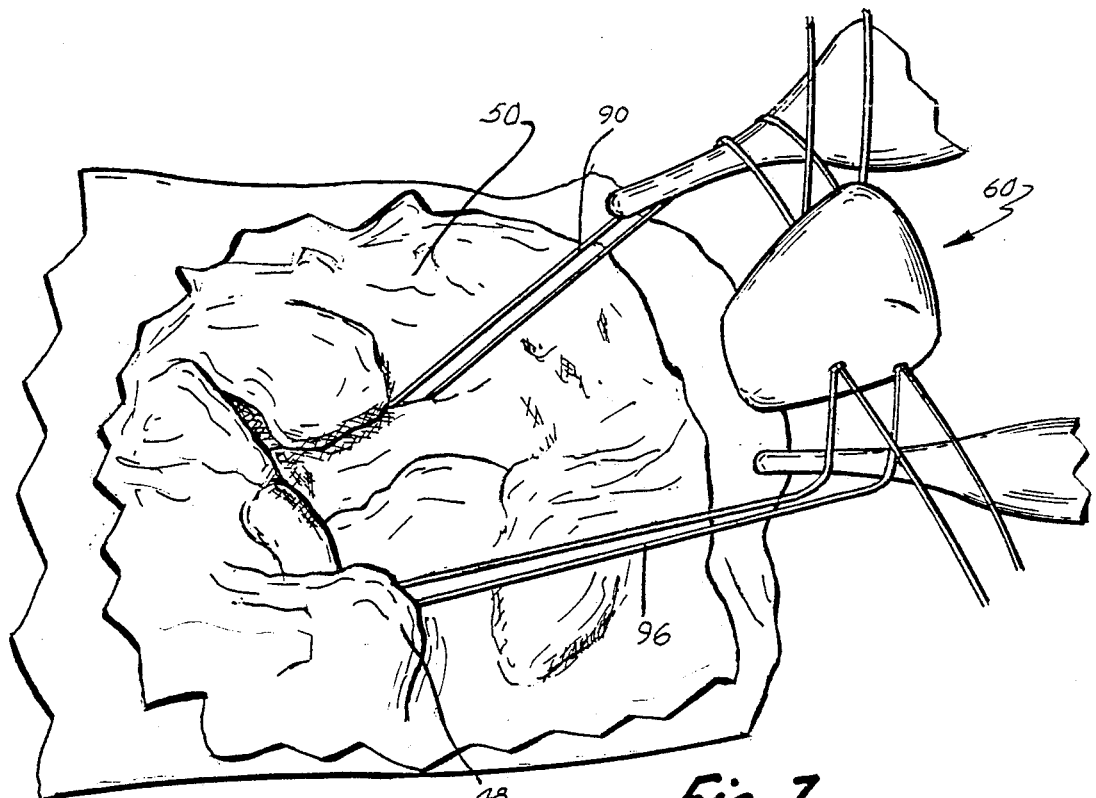

Stabilization of the implant in accordance with the present invention is illustrated in FIGS. 5–8. As shown in FIGS. 5 and 7, a first suture 90 having ends 92, 94 is stitched to a wrist ligament. The ligament is preferably the ulnolunate ligament 50, although others could be used. Ends 92, 94 are passed through suture passages 76, 78 and extend away from scaphoid face 66 of implant 60. A second suture 96 is stitched to another ligament, preferably the radioscapholunate ligament 48. Again, another ligament could be used. Suture 96 has ends 98, 100 which are passed through suture passages 76, 78 so that they extend away from the triquetrum face 64.

Figure 8:
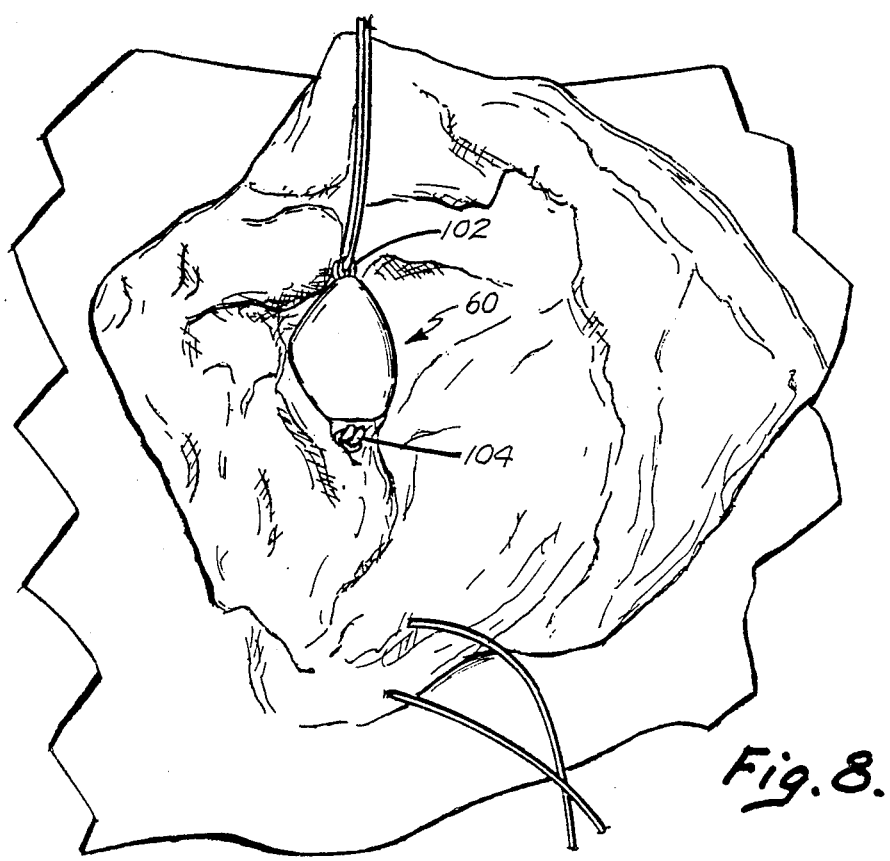

When the sutures have been passed through the implant body, as shown in FIG. 7, the ends 92, 94 and the ends 98, 100 may be grasped and pulled outwardly. This pulls the lunate downwardly and into the proper position in the proximal carpal row. As seen in FIGS. 6 and 8, the sutures are then tied and cut to define knots 102, 104.

The implant, the sutures, the attachment to the ligaments of the wrist insure that the implant is positioned and properly stabilized. Face 64 abuts against or is positioned to articulate with the triquetrum, and face 66 is positioned to articulate with the adjacent scaphoid bone. Capitate recess 70 is positioned to articulate with the head of the capitate bone.

The present invention provides a unique implant and method for stabilizing the implant which is fabricated from rigid material. The method employs two simple sutures and a pair of passage formed in the implant body. The implant and method in accordance with the present invention eliminates the stabilizing stem which can cause trauma to the bone. Erosion problems heretofore experienced are eliminated. Suturing the implant to the underlying ligaments provides stability using a relatively simple surgical procedure.

In view of the foregoing description, those of ordinary skill in the art may envision various modifications which would not depart from the inventive concepts disclosed herein. The above description should, therefore, be considered as only that of the preferred embodiment. The true spirit and scope of the present invention may be determined by reference to the appended claims.

The embodiments of the invention in which an exclusive property or privilege is claimed are defined as as follows:

1. An implant for replacement of the lunate bone, said implant comprising:
   a one-piece, at least semi-rigid body, said body defining:
   a planar triquetrum face;
   a planar scaphoid face;
   a cupped, concave, smooth distal surface;
   a proximal surface having a smooth, convex shape, said proximal surface joining proximal edges of said triquetrum and said scaphoid faces;
   a dorsal surface extending between dorsal edges of said triquetrum and scaphoid faces; and
   a palmar surface extending between palmar lateral surfaces of said triquetrum and scaphoid faces, said body further including a plurality of suture passages extending between and opening through said triquetrum and scaphoid faces.

2. An implant as defined by claim 1 wherein said suture passages extend in spaced, generally parallel relationship.

3. An implant as defined by claim 2 wherein one of said suture passages extends adjacent said dorsal surface and one of said suture passages extends adjacent said palmar surface.

4. An implant as defined by claim 3 further including:
   a pair of sutures, one of said sutures passing through said suture passages and including ends extending away from said triquetrum face and the other of said sutures passing through said suture passages and having ends extending away from said scaphoid face.

5. An implant as defined by claim 1 further including:
   a pair of sutures, one of said sutures passing through said suture passages and including ends extending away from said triquetrum face and the other of said sutures passing through said suture passages and having ends extending away from said scaphoid face.

* * * * *